US012708754B2

(12) United States Patent
Nakagami et al.

(10) Patent No.: US 12,708,754 B2
(45) Date of Patent: Aug. 18, 2026

(54) MEDICAL CONNECTOR

(71) Applicant: NIPRO CORPORATION, Osaka (JP)

(72) Inventors: Hiroyuki Nakagami, Osaka (JP); Minoru Aihara, Osaka (JP)

(73) Assignee: NIPRO CORPORATION, Osaka (JP)

( * ) Notice: Subject to any disclaimer, the term of this patent is extended or adjusted under 35 U.S.C. 154(b) by 599 days.

(21) Appl. No.: 18/036,990

(22) PCT Filed: Nov. 17, 2021

(86) PCT No.: PCT/JP2021/042197
§ 371 (c)(1),
(2) Date: May 15, 2023

(87) PCT Pub. No.: WO2022/107796
PCT Pub. Date: May 27, 2022

(65) Prior Publication Data

US 2024/0017050 A1 Jan. 18, 2024

(30) Foreign Application Priority Data

Nov. 17, 2020 (JP) ................................ 2020-190903

(51) Int. Cl.
*A61M 39/26* (2006.01)
*A61M 39/10* (2006.01)
*A61M 39/22* (2006.01)

(52) U.S. Cl.
CPC ............ *A61M 39/10* (2013.01); *A61M 39/22* (2013.01); *A61M 2039/1066* (2013.01)

(58) Field of Classification Search
CPC .................. A61M 39/10; A61M 39/26; A61M 2039/1072
See application file for complete search history.

(56) References Cited

U.S. PATENT DOCUMENTS

2007/0112311 A1 5/2007 Harding et al.
2011/0233435 A1 9/2011 Matsumoto et al.
(Continued)

FOREIGN PATENT DOCUMENTS

JP 2002-35140 A 2/2002
JP 2018-130501 A 8/2018
JP 2019-118518 A 7/2019
(Continued)

OTHER PUBLICATIONS

International Search Report dated Jan. 11, 2022, issued in counterpart International Application No. PCT/JP2021/042197, with English Translation. (4 pages).
(Continued)

*Primary Examiner* — Deanna K Hall
(74) *Attorney, Agent, or Firm* — WHDA, LLP

(57) ABSTRACT

A medical connector according to one embodiment of the present invention is provided with: a valve body which has a slit formed therein; a cylindrical outer housing which houses the valve body in the cylindrical shape thereof and retains the valve body therein; and a cylindrical inner housing which is inserted into the cylindrical shape of the outer housing so as to support an under surface of the valve body. A joint is formed between the valve body and the outer housing. The joint is positioned radially outward of the connector beyond the upper edge of the inner housing.

11 Claims, 10 Drawing Sheets

(56) References Cited

U.S. PATENT DOCUMENTS

| | | | | |
|---|---|---|---|---|
| 2017/0106182 | A1* | 4/2017 | Yoshioka | A61M 39/04 |
| 2019/0240473 | A1 | 8/2019 | Tsunoda et al. | |

FOREIGN PATENT DOCUMENTS

| | | | |
|---|---|---|---|
| WO | 2010/073643 | A1 | 7/2010 |
| WO | 2015/156272 | A1 | 10/2015 |

OTHER PUBLICATIONS

Extended (Supplementary) European Search Report dated Aug. 28, 2024, issued in counterpart EP Application No. 21894670.5. (9 pages).

* cited by examiner

MEDICAL CONNECTOR

TECHNICAL FIELD

The present invention relates to a medical connector including a valve body in which a slit is formed, and more particularly to a medical connector used for a fluid path in a medical field such as an intravenous line and a blood circuit for dialysis.

BACKGROUND

Hitherto, a medical connector to which a male connector such as a syringe can be connected has been used for a fluid path for administration of a medicine such as infusion, blood sampling, dialysis, and the like. For example, Patent Literature 1 discloses a medical connector including a valve body in which a slit is formed, a tubular housing that holds the valve body, and an annular pressing member. These medical connectors have a structure in which the valve body is coupled to the housing, and a circumferential edge portion of the valve body is sandwiched between the housing and the pressing member from opposite sides in a thickness direction. In addition, an annular groove is formed in the circumferential edge portion of the valve body, and a claw-like locking projection to be inserted into the groove is formed in the pressing member.

CITATION LIST

Patent Literature

Patent Literature 1: JP 2018-130501 A

SUMMARY

Technical Problem

The medical connector of Patent Literature 1 is used by inserting a male connector such as a syringe into the slit of the valve body. The male connector may be connected many times during the long-term use of the medical connector depending on medical treatment. In this case, the circumferential edge portion of the valve body may come off the locking projection of the pressing member and fall inward due to deformation of the valve body. As one means for preventing the coming-off of the circumferential edge portion of the valve body, it is conceivable to reduce a load applied to the circumferential edge portion of the valve body by applying a lubricant to the slit of the valve body to increase slipperiness between the male connector and the slit. However, the effect of the lubricant is reduced with the connection of the male connector, and a sliding resistance is increased. Therefore, it is difficult to prevent the coming-off of the circumferential edge portion of the valve body.

In addition, as a result of studies by the present inventors, it has been found that in a case where an upper extension portion of the valve body is formed in such a way as to surround an outer peripheral portion of the locking projection of the pressing member, if the apex of the upper extension portion is not constrained by the housing or the like, the upper extension portion is likely to come off the locking projection and fall inward when the valve body is pushed and deformed by the male connector inserted into the slit. In particular, in a case where the apex of the upper extension portion is biased toward a radially inner side of the extension portion, the upper extension portion is more likely to come off.

An object of the present invention is to provide a medical connector capable of more reliably suppressing coming-off of a valve body when a male connector is connected.

Solution to Problem

A medical connector according to an aspect of the present invention includes a valve body in which a slit is formed, a cylindrical external housing that houses the valve body and holds the valve body, and a cylindrical internal housing that is inserted into the cylindrical external housing and supports a lower surface of the valve body, in which a bonding portion is formed between the valve body and the external housing, and the bonding portion is positioned outside an upper end of the internal housing in a radial direction of the connector.

With the above configuration, since the valve body is bonded to the inner circumferential surface of the external housing, the valve body can be firmly fixed, and a circumferential edge portion of the valve body is suppressed from falling inside the connector when a male connector is connected. In addition, since the bonding portion is positioned outside the upper end of the internal housing in the radial direction of the connector, a force applied to the valve body when the male connector is connected is hardly applied to the bonding portion, and separation of the bonding portion is suppressed.

A medical connector according to another aspect of the present invention includes a valve body in which a slit is formed, a cylindrical external housing that houses the valve body and holds the valve body, a pressing member that is fixed to an upper end portion of the external housing, and a cylindrical internal housing that is inserted into the cylindrical external housing and supports a lower surface of the valve body, in which an outer circumferential surface of the valve body and an inner circumferential surface of the external housing are bonded to each other by insert molding or multicolor molding, and the pressing member is arranged in such a way as to surround an upper surface of the valve body in plan view.

With the above configuration, since the outer circumferential surface of the valve body is bonded to the inner circumferential surface of the external housing, a circumferential edge portion of the valve body is suppressed from falling inside the connector when the male connector is connected. When insert molding or multicolor molding is performed by injecting a resin used to form the valve body into a support member having a fine shape portion such as a small groove or gap, the resin is less likely to enter the fine shape portion, and air bubbles may remain. When air bubbles remain, the air bubbles are likely to cause separation, and the valve body is likely to be separated from the support member. On the other hand, with the above configuration, as the pressing member and the internal housing that are separate from the external housing are used, for example, the pressing member and the internal housing can be coupled after the valve body and the external housing are integrally molded. Therefore, the external housing can be formed in a simple shape, and a fine shape portion where air bubbles are likely to remain during insert molding can be eliminated. That is, air bubbles are less likely to be generated on a bonding surface between the valve body and the external housing, and a high bonding strength can be secured.

A medical connector according to another aspect of the present invention includes a valve body in which a slit is formed, a cylindrical external housing that houses the valve body and holds the valve body, and a cylindrical internal housing that is inserted into the cylindrical external housing and supports a lower surface of the valve body, in which the valve body includes a valve main body portion in which the slit is formed and an extension portion extending downward beyond a lower end of the valve main body portion and positioned between the external housing and the internal housing, and an outer circumferential surface of the extension portion and an inner circumferential surface of the external housing are bonded to each other.

With the above configuration, since the outer circumferential surface of the extension portion of the valve body is bonded to the inner circumferential surface of the external housing, the bonding area is large, a strong fixing force of the valve body with respect to the external housing is applied, and a circumferential edge portion of the valve body is suppressed from falling inside the connector when the male connector is connected.

A medical connector according to another aspect of the present invention includes a valve body in which a slit is formed, a cylindrical external housing that houses the valve body and holds the valve body, and a cylindrical internal housing that is inserted into the external housing and supports a lower surface of the valve body, in which an outer circumferential surface of the valve body and an inner circumferential surface of the external housing are bonded to each other, a part of the valve body is inserted into the cylindrical internal housing, and the outer circumferential surface of the valve body and an inner circumferential surface of the internal housing are not bonded to each other.

With the above configuration, since the outer circumferential surface of the valve body is bonded to the inner circumferential surface of the external housing, a circumferential edge portion of the valve body is suppressed from falling inside the connector when the male connector is connected. On the other hand, since an outer circumferential surface of the portion of the valve body inserted into the cylindrical internal housing is not bonded to the inner circumferential surface of the internal housing, a resistance when the male connector is connected is reduced, and a connection operation for the male connector becomes smoother. In a case where the outer circumferential surface of the valve body and the inner circumferential surface of the internal housing are bonded, the bonding portion is separated by deformation of the valve body when the male connector is connected, but at that time, a force for separating the bonding portion is required, and a resistance increases.

A medical connector according to another aspect of the present invention includes a valve body in which a slit is formed, and a cylindrical housing that houses the valve body and holds the valve body, in which an engagement projection is provided at an upper end portion of the housing, the valve body includes a valve main body in which the slit is formed, an upper groove into which the engagement projection is inserted, and an upper extension portion extending in such a way as to face an outer circumferential surface of the valve main body with the upper groove interposed therebetween, an apex of the upper extension portion is formed outside a center of the upper extension portion in a width direction, and an outer circumferential surface of the upper extension portion and an inner circumferential surface of the housing are bonded to each other.

With the above configuration, since the upper extension portion is bonded to the inner circumferential surface of the housing and the apex of the upper extension portion is formed outside the center of the upper extension portion in the width direction, extension of the upper extension portion is suppressed compared with a case where the apex of the upper extension portion is biased toward a radially inner side of the extension portion, and the coming-off of the upper extension portion can be more effectively suppressed. Specifically, in a case where the apex of the upper extension portion is biased toward the radially inner side of the extension portion, the radially inner side of the upper extension portion becomes thick in an axial direction, and when being pulled radially inward by the male connector, the thick portion extends and is partially displaced toward an inner side of the engagement projection, and thus there is a possibility of a phenomenon occurring where the portion displaced toward the inner side of the engagement projection is caught on the inner side of the engagement projection and does not return to an outer side of the engagement projection.

In the medical connector according to the present invention, the valve body and the external housing are preferably integrally molded. In this case, it is easy to increase a bonding strength between the valve body and the external housing, and separation of the bonding portion is further suppressed. Therefore, it is possible to more effectively suppress coming-off of the valve body when the male connector is connected.

In the medical connector according to the present invention, it is preferable that a groove into which the upper end portion of the internal housing is inserted is formed in the lower surface of the valve body, and the groove is formed inside an outer edge of a portion of the valve body exposed to the outside in the radial direction of the connector. In this case, when the male connector is connected, the valve body is deformed at a portion where the groove is formed, and a force applied to the bonding portion becomes small. Therefore, it is possible to more effectively suppress coming-off of the valve body when the male connector is connected.

Advantageous Effects of Invention

With the medical connector according to the present invention, it is possible to more reliably prevent the valve body from coming off when the male connector is connected.

DESCRIPTION OF EMBODIMENTS

Hereinafter, an example of embodiments of a medical connector according to the present invention will be described in detail with reference to the drawings. The embodiments described below are merely examples, and the present invention is not limited to the following embodiments. In addition, it is assumed from the beginning that components of the plurality of embodiments and modifications described below are selectively combined.

First Embodiment

Figure 1:
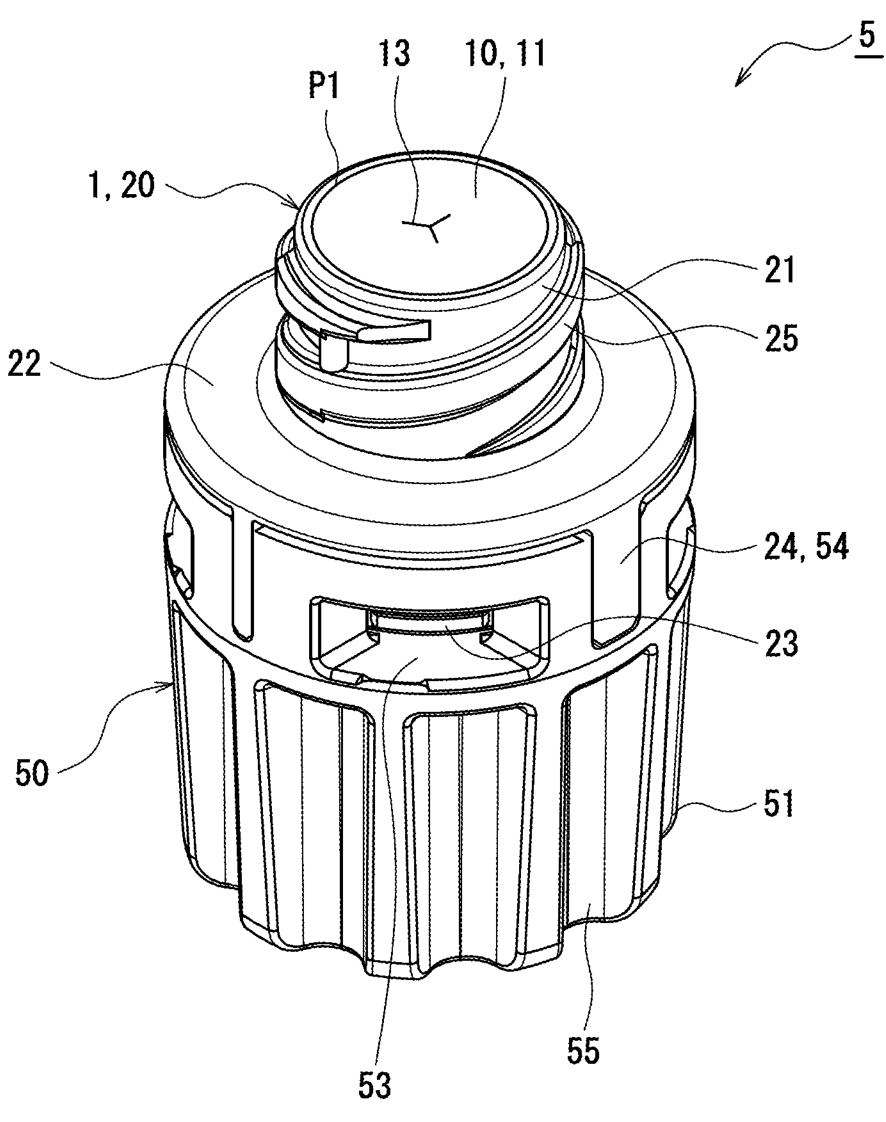
FIG. 1 is a perspective view of a medical connector according to a first embodiment.
Figure 2:
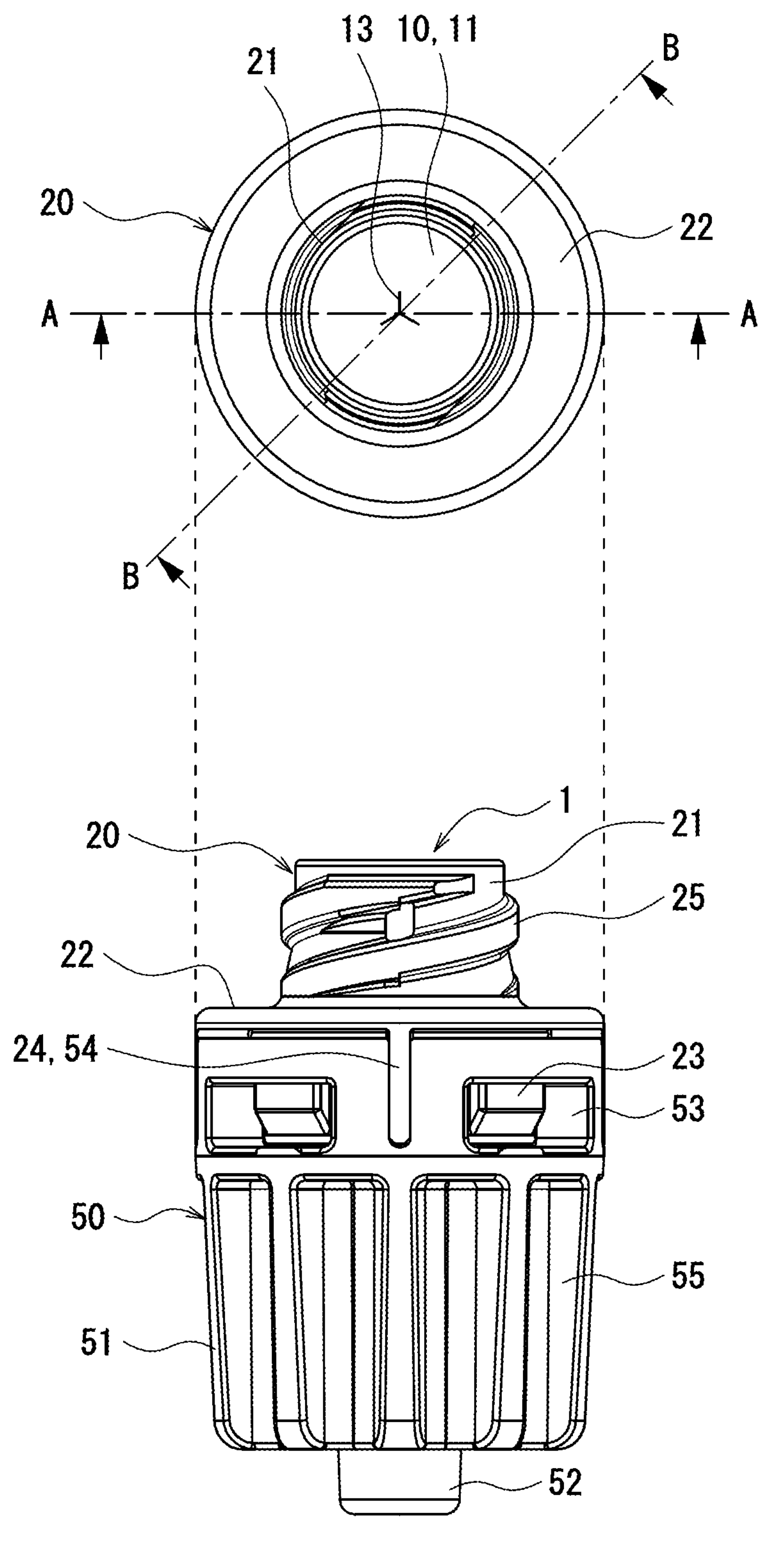
FIG. 2 is a plan view and a front view of a medical connector according to a second embodiment.
Figure 3:
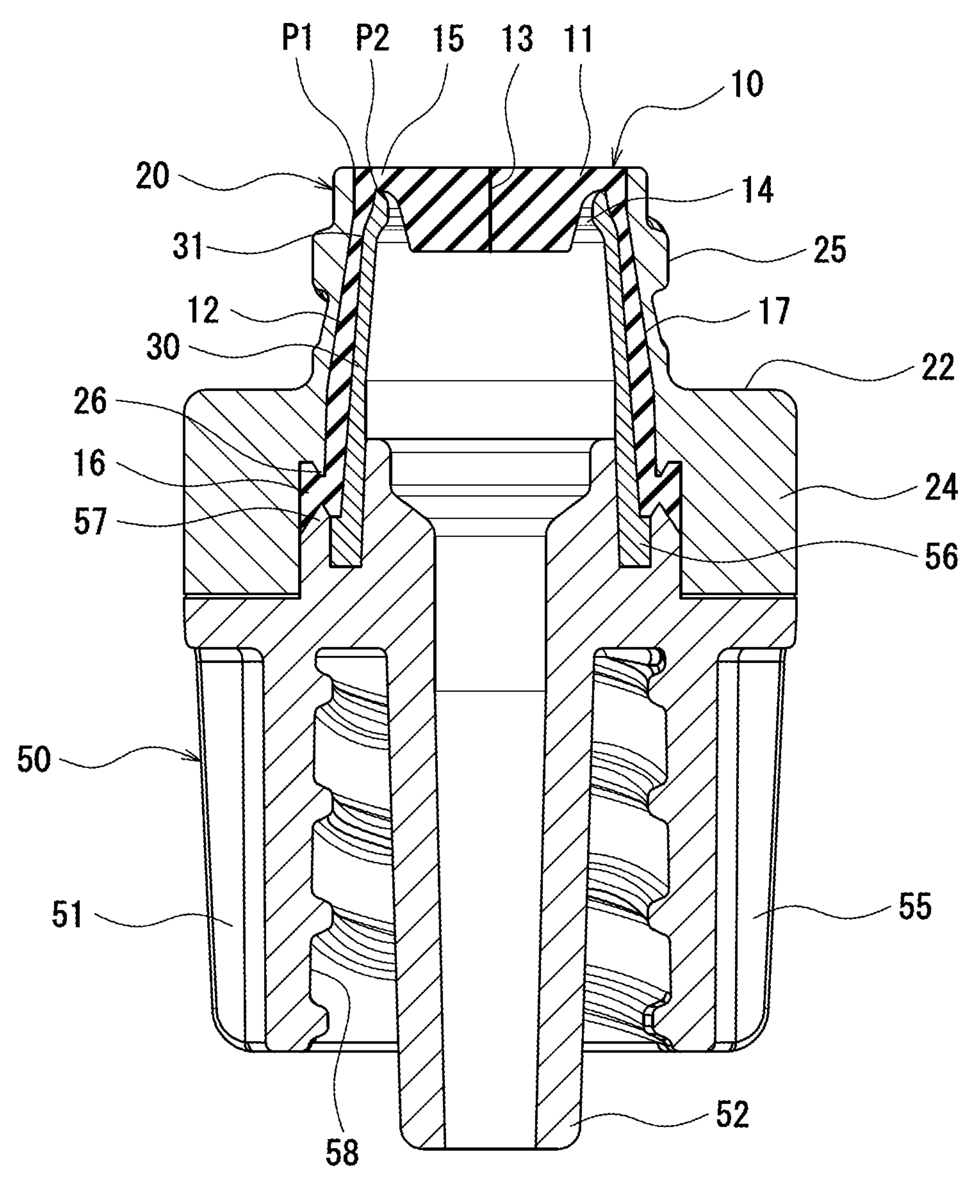
FIG. 3 is a cross-sectional view taken along line AA in FIG. 2.
Figure 4:
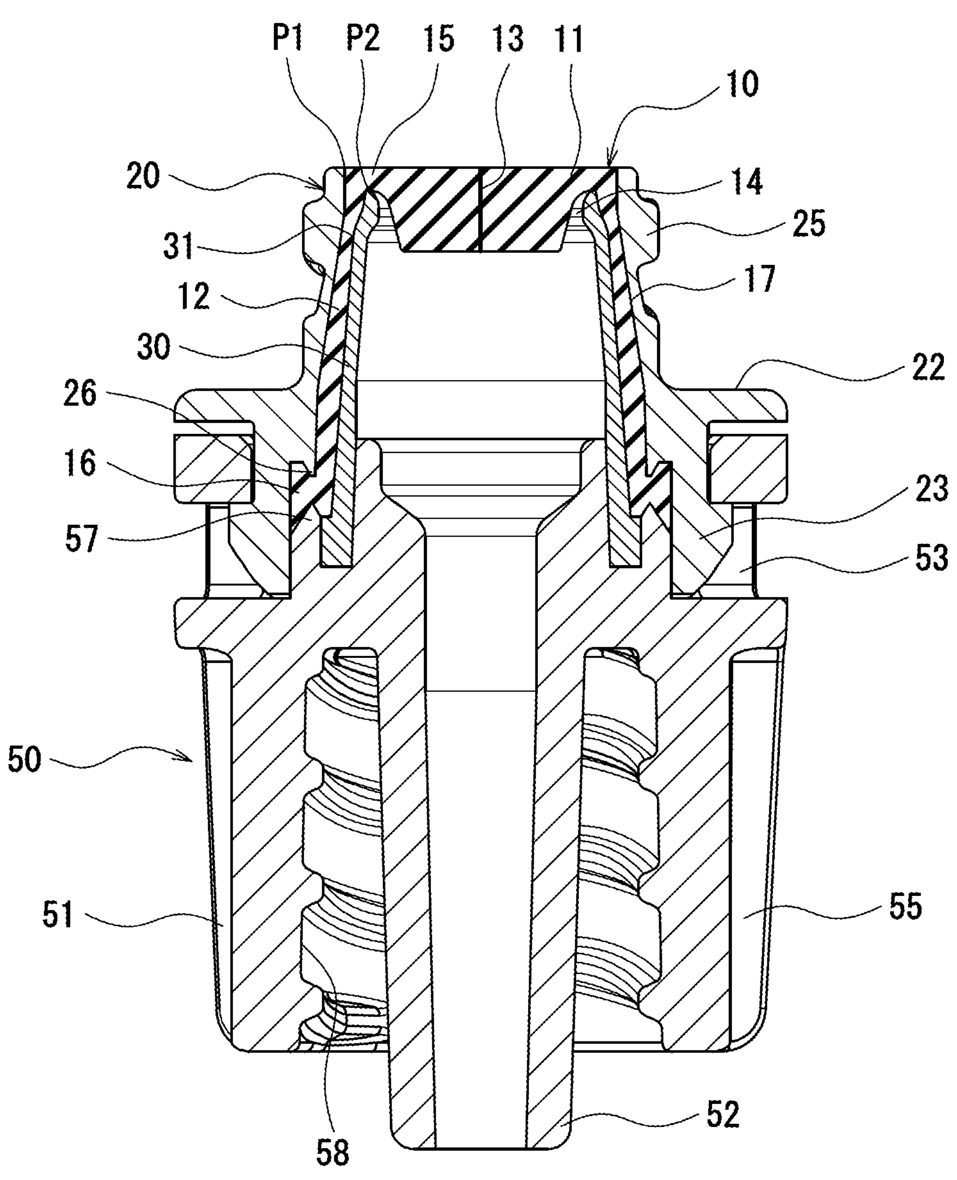
FIG. 4 is a cross-sectional view taken along line BB in FIG. 2.

A medical connector 1 according to a first embodiment will be described in detail below with reference to FIGS. 1 to 6. FIG. 1 is a perspective view of the medical connector 1, and FIG. 2 is a plan view and a front view of the medical connector 1. FIG. 3 is a cross-sectional view taken along line AA in FIG. 2, and FIG. 4 is a cross-sectional view taken along line BB in FIG. 2.

As illustrated in FIGS. 1 to 4, the medical connector 1 includes a valve body 10, a cylindrical external housing 20 that houses the valve body 10 and holds the valve body 10, and a cylindrical internal housing 30 that is inserted into the cylindrical external housing and supports a lower surface of the valve body 10. A slit 13 that enables insertion of a male connector such as a syringe 100 (see FIG. 5 described below) having no metal needle is provided in the valve body 10. The slit 13 is closed in a state where the male connector is not connected, and the valve body 10 closes an upper end opening of the external housing 20. The external housing 20 and the internal housing 30 are cylindrical bodies whose upper and lower ends (opposite ends in an axial direction) are opened.

In the present specification, a direction along the axial direction of the external housing 20 is referred to as a "vertical direction" of the medical connector 1 and each component of the connector, and a side on which a valve main body portion 11 of the valve body 10 in which the slit 13 is formed is arranged is referred to as an "upper side". The external housing 20 and the internal housing 30 are arranged in such a way that axial directions thereof coincide with each other.

The medical connector 1 is a female connector connected by inserting the male connector into the slit 13 of the valve body 10. The valve body 10 is, for example, an elastic body formed of silicone rubber, and is configured to be elastically deformed when being pushed downward to open the slit 13 when a distal end portion of the male connector is inserted into the slit 13. In addition, when the distal end portion of the male connector is pulled out from the valve body 10, the valve body 10 returns to its original shape, and the slit 13 is closed. The medical connector 1 is a so-called needleless connector to which the male connector having no metal needle can be connected.

As will be described in detail below, an outer edge of a portion of the valve body 10 exposed to the outside is positioned outside an upper end P2 of the internal housing 30 in a radial direction of the medical connector 1 and is bonded to an inner circumferential surface of the external housing 20. Here, the outer edge of the portion of the valve body exposed to the outside is an upper end P1 of an outer circumferential surface in the present embodiment. A bonding portion 17 between the valve body 10 and the external housing 20 is positioned outside the upper end P2 of the internal housing 30 in the radial direction of the connector, and is configured not to be separated when the male connector is connected. Therefore, coming-off of the valve body 10 can be effectively suppressed, and infiltration of a medicinal solution or the like into a space between the valve body 10 and the external housing 20 is suppressed.

In the present embodiment, a medical plug 5 including the medical connector 1 and a plug base 50 is configured by attaching the medical connector 1 to the plug base 50. The medical plug 5 is a connecting device used for connecting an intravenous line, a blood circuit, a blood access catheter, and the like. In the medical plug 5, a lower end opening of the medical connector 1 is connected to an upper end opening of an inner cylindrical portion 52 of the plug base 50. The medical plug 5 may be attached to a T-shaped tube base 60 illustrated in FIG. 10 described below or a three-way stopcock base 70 illustrated in FIG. 11.

The plug base 50 includes an outer cylindrical portion 51 and the inner cylindrical portion 52, and has a structure in which a flow path through which a medicinal solution or the like flows is formed inside the inner cylindrical portion 52. The inner cylindrical portion 52 is a male luer portion to be inserted into a female connector (not illustrated), and has a tapered shape where an outer diameter gradually decreases toward a lower end. The outer cylindrical portion 51 has an inner diameter lamer than the outer diameter of the inner cylindrical portion 52 and is arranged in such a way as to surround the inner cylindrical portion 52. A spiral lock groove 58 is formed on an inner circumferential surface of the outer cylindrical portion 51. The female connector to which the inner cylindrical portion 52 is connected is inserted between the outer cylindrical portion 51 and the inner cylindrical portion 52, for example, and is connected to the plug base 50 by using the lock groove 58.

The plug base 50 is formed of a hard resin material. The resin used to form the plug base 50 is, for example, polyolefin such as polypropylene, and may be polycarbonate, polyethylene terephthalate, polyvinyl chloride, or the like, and is not particularly limited. The outer cylindrical portion 51 and the inner cylindrical portion 52 are integrally molded and are connected to each other at an upper portion of the plug base 50. An upper end of the inner cylindrical portion 52 is positioned in such a way as to be aligned with an upper end of the outer cylindrical portion 51 in the radial direction, while the lower end of the inner cylindrical portion 52 protrudes downward beyond a lower end of the outer cylindrical portion 51.

An opening portion 53 and a first groove 54 are formed in an upper portion of the outer cylindrical portion 51. The opening portion 53 is a portion into which a locking claw 23 of the medical connector 1 is inserted, penetrates through a cylinder wall of the outer cylindrical portion 51, and is used for connecting the medical connector 1 and the plug base 50. Considering that the external housing 20 is bonded to the valve body 10, a material of the external housing 20 is limited. Furthermore, in a case where the medical connector 1 and the plug base 50 are welded or fixed with an adhesive, a material of the plug base 50 is also limited. As the medical connector 1 and the plug base 50 are physically connected, it is possible to mold the plug base 50, which is a member that contacts liquid, with a preferable material. A plurality of opening portions 53 are formed in a circumferential direction of the outer cylindrical portion 51. Further, the first groove 54 extending in the vertical direction from the upper end of the outer cylindrical portion 51 is formed between the opening portions 53. A projection 24 of the medical connector 1 is inserted into the first groove 54.

A recess 55 extending long in the vertical direction is formed on an outer circumferential surface of the outer cylindrical portion 51. A plurality of recesses 55 extend from a central portion in the vertical direction to the lower end of the outer cylindrical portion 51 and are formed in the circumferential direction of the outer cylindrical portion 51. When the medical plug 5 and the female connector are connected, for example, a portion of the outer cylindrical portion 51 where the recesses 55 are formed is gripped and rotated. As the plurality of recesses 55 are provided, unevenness is formed in a lower portion of the outer cylindrical portion 51, so that ease of gripping the plug base is improved.

An upper end portion of the inner cylindrical portion 52 has a tapered shape where an outer diameter gradually decreases from a portion connected to the outer cylindrical portion 51 toward the upper end. In the present embodiment, the upper end portion of the inner cylindrical portion 52 is inserted into the cylindrical internal housing 30 of the medical connector 1. Since the internal housing 30 gradually decreases in diameter from a lower end toward the upper end P2, it is preferable that the upper end portion of the inner cylindrical portion 52 has a tapered shape that matches the shape of the internal housing 30. An inner diameter of the inner cylindrical portion 52 increases near the upper end.

In the upper portion of the plug base 50, an annular second groove 56 is formed between the outer cylindrical portion 51 and the inner cylindrical portion 52 in such a way as to surround the inner cylindrical portion 52. In the present embodiment, a lower end portion of the internal housing 30 is inserted into the second groove 56. A protrusion 57 is formed outside the second groove 56. The protrusion 57 is formed in an annular shape in such a way as to surround the second groove 56. The protrusion 57 presses a lower end portion of the valve body 10 and holds the lower end portion of the valve body 10 between the protrusion 57 and the external housing 20. The protrusion 57 may have a flat distal end portion. It is preferable that the distal end portion has two inclined surfaces and is pointed, so that the valve body 10 can be more strongly compressed. A gap into which the locking claw 23 of the medical connector 1 can be inserted is formed between the outer cylindrical portion 51 and the protrusion 57.

As described above, the medical connector 1 includes the valve body 10, the external housing 20, and the internal housing 30. Hereinafter, each component of the medical connector 1 will be described in detail.

[Valve Body 10]

As described above, the valve body 10 is a member that includes the slit 13 penetrating through the valve body 10 and is elastically deformed when the male connector such as the syringe 100 is inserted into the slit 13. The valve body 10 is inserted into the cylindrical external housing 20, is supported by the internal housing 30, and is in close contact with each housing. The valve body 10 is preferably formed of a material containing an elastomer, preferably, a thermosetting elastomer. For example, the valve body 10 is formed of a synthetic rubber such as a butadiene rubber, a nitrile rubber, an isoprene rubber, a fluoro rubber, a styrene-based rubber, or a silicone rubber. Among them, the styrene-based rubber and the silicone rubber are preferable from the viewpoint of bondability to the external housing 20 at the time of injection molding.

The valve body 10 includes the valve main body portion 11 in which the slit 13 is formed, and an extension portion 12 formed on an outer circumferential side of the valve main body portion 11. The valve main body portion 11 is formed in a substantially disk shape, and has a size sufficient to close the upper end opening of the external housing 20 with the valve main body portion 11 and a valve outer circumferential portion. Upper surfaces of the valve main body portion 11 and the valve outer circumferential portion have a perfect circular shape, are flat in the radial direction of the external housing 20, and are flush with an upper end of the external housing 20. The entire upper surface of the external housing 20 is exposed and is not covered with the external housing 20 or other members.

The valve main body portion 11 and the valve outer circumferential portion can seal the upper end opening of the external housing 20, and have a thickness that does not interfere with insertion of the male connector. An example of the thickness of the valve main body portion 11 is 0.5 mm to 2 mm. The slit 13 is formed to penetrate through the valve main body portion 11 in a thickness direction at a central portion of the valve main body portion 11 in the radial direction. The slit 13 is formed in a thin line shape in plan view. In the present embodiment, three slits 13 are formed at equal intervals in the radial direction from the center of the upper surface of the valve main body portion 11, but the length, number, and the like, of the slits 13 are not particularly limited. The slits 13 may be formed as one straight line in plan view, or four or more slits may be formed radially.

An outer circumferential surface of the valve body 10 is bonded to the inner circumferential surface of the external housing 20 and is in close contact with the inner circumferential surface of the external housing 20 firmly enough to prevent separation even when the male connector is connected. The bonding portion 17 between the valve body 10 and the external housing 20 is formed at least at an upper end portion of the outer circumferential surface of the valve body 10. In the present embodiment, the bonding portion 17 is formed from the upper end (the upper end P1 of the outer circumferential surface) of the valve body 10 to the lower end of the extension portion 12. The bonding portion 17 may be formed of an adhesive, but it is preferable that the bonding portion 17 is formed by injection molding. The valve body 10 and the external housing 20 are preferably integrally molded.

A groove 14 into which an upper end portion of the internal housing 30 is inserted is formed in a lower surface of the valve body 10. The valve main body portion 11 is thick, and a portion where the groove 14 is formed is a thin portion 15 having a thickness smaller than other portions. The upper end P2 of the internal housing 30 is in contact with the thin portion 15 at the innermost portion of the groove 14. When the male connector is inserted into the slit 13, the valve body 10 is elastically deformed by being bent at the thin portion 15.

The groove 14 is formed in an annular shape in the circumferential direction at a circumferential edge portion of the lower surface of the valve main body portion 11. The groove 14 is formed inside the upper end P1 of the outer circumferential surface of the valve body 10 in the radial direction of the medical connector 1. In other words, the upper end P1 of the outer circumferential surface of the valve body 10 is positioned outside the groove 14 in the radial direction of the valve body 10. In this case, when the male connector is connected, hardly any force is applied to the upper end portion of the outer circumferential surface of the valve body 10, and separation of the bonding portion 17 is effectively suppressed. An upper end of the groove 14 is positioned higher than a central portion of the valve main body portion 11 in the axial direction, and a large space is formed in the groove 14. Therefore, a distance between the valve body 10 that comes into contact with an inner surface of the internal housing 30 when the male connector is inserted can be increased, an insertion resistance can be reduced, and a load applied to a circumferential edge of the valve body 10 can be reduced. On the other hand, since the valve main body portion 11 on the inner side with respect to the groove 14 is thick, an outer circumferential surface of the male connector can be firmly sealed.

The valve body 10 is arranged in a state where a portion surrounded by the groove 14 is inserted into the cylindrical internal housing 30. The groove 14 is formed in a substantially inverted V shape in a cross-sectional view, and the portion of the valve body 10 inserted into the cylindrical internal housing 30 has a tapered shape where a diameter gradually decreases toward the lower end. An inner diameter of the internal housing 30 gradually increases from the upper end P2 toward the lower end. Therefore, when the male connector is inserted, a space in which the valve main body portion 11 is displaced outward is formed between the valve main body portion 11 and an inner circumferential surface of the internal housing 30, and the presence of this space reduces an insertion resistance of the male connector.

In the present embodiment, a part of the valve main body portion 11 is inserted into the cylindrical internal housing 30 as described above, but there is a large gap between an outer circumferential surface of the valve main body portion 11 and the inner circumferential surface of the internal housing 30, and the outer circumferential surface of the valve main body portion 11 and the inner circumferential surface of the internal housing 30 are not bonded to each other. In this case, compared with a form where the outer circumferential surface of the valve main body portion 11 and the inner circumferential surface of the internal housing are bonded, a force for separating the bonding portion at the time of connection of the male connector is not required, and thus, a resistance at the time of connection is reduced, and a connection operation for the male connector becomes smoother. In the present embodiment, the valve body 10 and the internal housing 30 are not bonded, but the valve body 10 and the internal housing 30 may be bonded. In this case, since the groove 14 is large, a bonding part between the inner surface of the internal housing 30 and the outer circumferential surface of the valve main body portion 11 can be minimized, and a problem of elastic deformation of the valve body being hindered by the bonding portion can be reduced.

The extension portion 12 is a portion formed at the valve outer circumferential portion and extending downward, and is formed in a substantially cylindrical shape. From the viewpoint of increasing a bonding area with the external housing 20, the extension portion 12 preferably extends downward from the valve main body portion 11. A length of the extension portion 12 in the vertical direction is larger than a length of the center of the valve main body portion 11 in the vertical direction. A diameter of the extension portion 12 is preferably larger than an outer diameter of the valve main body portion 11. The diameter of the extension portion 12 is preferably larger than a diameter of a portion of the valve body 10 that is exposed to the outside. The diameter of the extension portion 12 is preferably larger than an outer diameter of the valve body 10. The length of the extension portion 12 in the vertical direction is larger than the thickness of the valve main body portion 11, the extension portion 12 extends to the vicinity of the lower ends of the external housing 20 and the internal housing 30, and an outer circumferential surface of the extension portion 12 is bonded to the inner circumferential surface of the external housing 20. As such an extension portion 12 is provided, the bonding area can be increased, graspability of the valve body 10 is improved, and a bonding state between the valve body 10 and the external housing 20 can be favorably maintained.

Similarly to the internal housing 30, the extension portion 12 has a shape where an inner diameter and an outer diameter gradually increase from the upper end toward the lower end. The extension portion 12 is bonded to the inner circumferential surface of the external housing 20, but is not bonded to the internal housing 30. The extension portion 12 is sandwiched between the external housing 20 and the internal housing 30, and is in close contact with an outer circumferential surface of the internal housing 30. A lower portion of the extension portion 12 is inserted into the upper portion of the plug base 50 together with the external housing 20 and the internal housing 30.

A projection 16 projecting radially outward is formed at a lower end portion of the extension portion 12. The projection 16 is preferably formed in an annular shape in a circumferential direction of the extension portion 12. In the present embodiment, the projection 16 and the external housing 20 are bonded to increase the bonding area. A groove is formed on an upper surface of the projection 16, and an inner surface of the external housing 20 is bonded to an outer surface of the groove. A lower surface of the projection 16 is flat and is depressed by being pressed by the protrusion 57 of the plug base 50. The projection 16 is pressed from above and below by the protrusion 57 and a protrusion 26 of the external housing 20. Since the projection 16 is strongly sandwiched between the external housing 20 and the plug base 50, the graspability of the valve body 10 is further improved. A portion of the valve body 10 above the extension portion 12 extends to an upper end of the medical connector 1, and is bonded to the external housing extending to the upper end of the medical connector 1. That is, an upper side of the valve body 10 is also bonded to the external housing 20. The bonding portion 17 is formed radially outside the slit 13 of the valve body 10, and the bonding area is large.

[External Housing 20]

The external housing 20 is a cylindrical member having upper and lower ends opened, covers the outer circumferential surface of the valve body 10, and holds the valve body 10 together with the internal housing 30. The valve body 10 does not protrude from both the upper and lower ends of the external housing 20, and the entire valve body is housed in the cylindrical external housing 20. The external housing 20 is formed of a hard resin material. Examples of the resin used to form the external housing 20 include polycarbonate, polybutylene terephthalate, polyethylene terephthalate, polyether ether ketone, polyphenylene ether, polyphenylene oxide, polyamide, and polyolefin. Among them, polybutylene terephthalate, polyethylene terephthalate, and polyamide are preferable.

The external housing 20 has a small-diameter portion 21 and a large-diameter portion 22. The small-diameter portion 21 is a portion having an outer diameter smaller than that of the large-diameter portion 22, and is formed at an upper portion of the external housing 20. Similarly to the valve body 10 and the internal housing 30, the small-diameter portion 21 has a shape where an inner diameter and the outer diameter gradually increase from the upper end to the lower end. A screw thread 25 is formed on an outer circumferential surface of the small-diameter portion 21. The screw thread 25 is used to lock the male connector connected to the medical connector 1.

In the large-diameter portion 22, the locking claw 23 and the projection 24 are formed. As described above, the locking claw 23 and the projection 24 are used for connection to the plug base 50. A plurality of locking claws 23 and a plurality of projections 24 are alternately formed in a circumferential direction of the large-diameter portion 22. The locking claw 23 extends in the vertical direction and has a shape where a lower portion projects radially outward. The locking claw 23 is inserted between the outer cylindrical portion 51 and the protrusion 57 of the plug base 50, and the lower portion of the locking claw 23 is inserted into the opening portion 53 of the outer cylindrical portion 51 and caught on an upper edge portion of the opening portion 53. The projection 24 is a portion to be inserted into the second groove 56 of the outer cylindrical portion 51 and is formed in a plate shape parallel to the vertical direction and the radial direction.

In the large-diameter portion 22, the protrusion 26 protruding downward is formed radially inside the locking claw 23 and the projection 24. The protrusion 26 is formed in, for example, an annular shape in a circumferential direction of the external housing 20. The protrusion 26 is arranged in such a way as to vertically overlap with the protrusion 57 of the plug base 50, and increases a bonding area with the valve body 10. After the coupling, the protrusion 26 holds the projection 16 of the valve body 10 between the protrusion 26 and the protrusion 57. The protrusion 26 has a pointed distal end so that the protrusion 57 and the protrusion 26 can easily compress the projection 16.

In the present embodiment, the valve body 10 and the external housing 20 are configured as an integrally molded product (hereinafter, referred to as an “integrally molded product (Z)”). The entire outer circumferential surface of the valve body 10 in contact with the inner circumferential surface of the external housing 20 from the upper end of the valve body 10 to the lower end of the projection 16 corresponds to the bonding portion 17. The bonding portion 17 has, for example, a substantially constant bonding strength (separation strength) over the entire region. It is preferable that the bonding portion 17 has a bonding strength sufficient to not be separated when the male connector is inserted into the slit 13 and the valve body 10 is elastically deformed. The valve body 10 is also bonded to the protrusion 26. As the protrusion 26 is provided, the area of the bonding portion 17 can be increased.

The integrally molded product (Z) is produced by, for example, insert molding. In this case, the resin used to form the valve body 10 is injected into the external housing 20 set in an injection molding mold and is integrated with the external housing 20. As a specific example, the external housing 20 formed of polyethylene terephthalate or polycarbonate is set in the mold, and two-part curable liquid silicone rubber is injected into the mold as the resin used to form the valve body 10. A melting point (softening point) of the resin used to form the external housing 20 is preferably higher than a molding temperature of the valve body 10. The liquid silicone rubber is cured and molded into the valve body 10 strongly adhering to the inner circumferential surface of the external housing 20, so that the integrally molded product (Z) in which the valve body 10 and the external housing 20 are integrated is obtained. The integrally molded product (Z) can also be produced by other molding methods such as insert molding and multicolor molding (particularly, two-color molding).

In the portion of the valve body 10 exposed to the outside, as described above, the upper end portion of the outer circumferential surface is positioned closer to the upper end of the medical connector 1 than the upper end P2 of the internal housing 30 inserted into the groove 14 of the valve main body portion 11 is, and is positioned radially outside the upper end P2, and is bonded to the inner circumferential surface of the external housing 20. In the present embodiment, the valve body 10 and the external housing 20 are the integrally molded product (Z), and the entire contact surface of each member corresponds to the bonding portion 17 having a substantially constant bonding strength. However, only the upper end portion of the outer circumferential surface of the valve body 10 may be bonded to the external housing 20, or a bonding strength of the upper end portion may be higher than that of other portions. An annular portion extending radially inward may be provided at an upper end portion of the external housing 20.

In the present embodiment, the entire outer circumferential surface of the valve body including the upper end P1 of the outer circumferential surface of the valve body 10 (the outer edge of the portion exposed to the outside of the valve body 10) is bonded to the inner circumferential surface of the external housing 20. In this case, the valve body 10 is stably held, and infiltration of a medicinal solution or the like into a space between the valve body 10 and the external housing 20 is easily suppressed. The annular groove 14 and the thin portion 15 are formed at the circumferential edge portion of the valve main body portion 11, and the upper end P1 is positioned radially outside the groove 14 and the thin portion 15. A configuration in which a non-bonding portion exists at the upper end of the outer circumferential surface of the valve body is understood to be equivalent to the present invention as long as the object of the present invention is not impaired.

A diameter of an upper surface of the valve body 10 and an inner diameter of the upper end of the external housing 20 are larger than an outer diameter of the upper end P2 of the internal housing 30, and the entire outer edge of the upper surface of the valve body is positioned outside the upper end P2 of the internal housing 30 in the radial direction of the medical connector 1. At the upper end of the medical connector 1, the annular bonding portion 17 is formed along an outer edge of the upper surface of the valve body 10. Since the outer diameter of the valve body 10 (extension portion 12) and an inner diameter of the external housing 20 increase from the upper end to the lower end, the entire bonding portion 17 is positioned radially outside the upper end P2 of the internal housing 30.

[Internal Housing 30]

The internal housing 30 is a cylindrical member having upper and lower ends opened, has an outer diameter smaller than the inner diameter of the external housing 20, and is arranged in the cylindrical external housing 20. The internal housing 30 is inserted into the extension portion 12 of the valve body 10 formed in a cylindrical shape, and the upper end portion thereof is inserted into the groove 14 of the valve body 10 and is in contact with the thin portion 15. The internal housing 30 presses the valve body 10 from the inside and holds the valve body 10 between the internal housing 30 and the external housing 20. The male connector such as the syringe 100 is inserted into the cylindrical internal housing 30. Therefore, the inner diameter of the internal housing 30 is larger than an outer diameter of an insertion portion of the male connector to be connected.

The internal housing 30 is formed of a hard resin material. The internal housing 30 may be formed of the same resin as the external housing 20 or may be formed of a different resin. The internal housing 30 is not integrally molded with the valve body 10 and is in close contact with the inner circumferential surface of the valve body 10, but is not bonded to the valve body 10. Therefore, it is not necessary to select the resin material in consideration of bonding to the valve body 10. In the present embodiment, the lower end portion of the internal housing 30 extends to be lower than the extension portion 12 of the valve body 10 and is inserted into the second groove 56 of the plug base 50. When the internal housing is coupled to the integrally molded external housing and valve body, a state in which only a portion in the vicinity of the upper end P2 is not bonded may be implemented by fixing the internal housing with an adhesive or the like except for the portion in the vicinity of the upper end P2. The internal housing may include two members, upper and lower members, and a state in which only the upper member is not bonded to the valve body 10 can also be implemented.

The internal housing 30 gradually increases in diameter from the upper end P2 toward the lower end, but the degree of increase in diameter is high at the upper end portion. A step 31 is formed at the upper end portion of the internal housing 30, and the degree of increase in diameter changes with the step 31 as a boundary. The step 31 is formed in an annular shape above a position corresponding to a lower end of the valve main body portion 11, for example. By increasing the degree of increase in diameter at the upper end portion of the internal housing 30, a large space for the valve body 10 deformed by the connection of the male connector to escape can be secured, and the insertion resistance of the male connector can be reduced. An inner surface of the upper end portion of the internal housing 30 increases in diameter toward the upper side. Therefore, even in a case where an outer circumferential side of the portion of the valve body 10 exposed to the outside is positioned outside the upper end P2 of the internal housing 30, the male connector can be guided to the inside. Since the inner surface of the upper end portion of the internal housing 30 has a curved shape in which an edge is hardly formed, a problem of the valve body 10 being sandwiched between the internal housing 30 and the male connector, and then being cut by an insertion load of the male connector is reduced.

Figure 5:
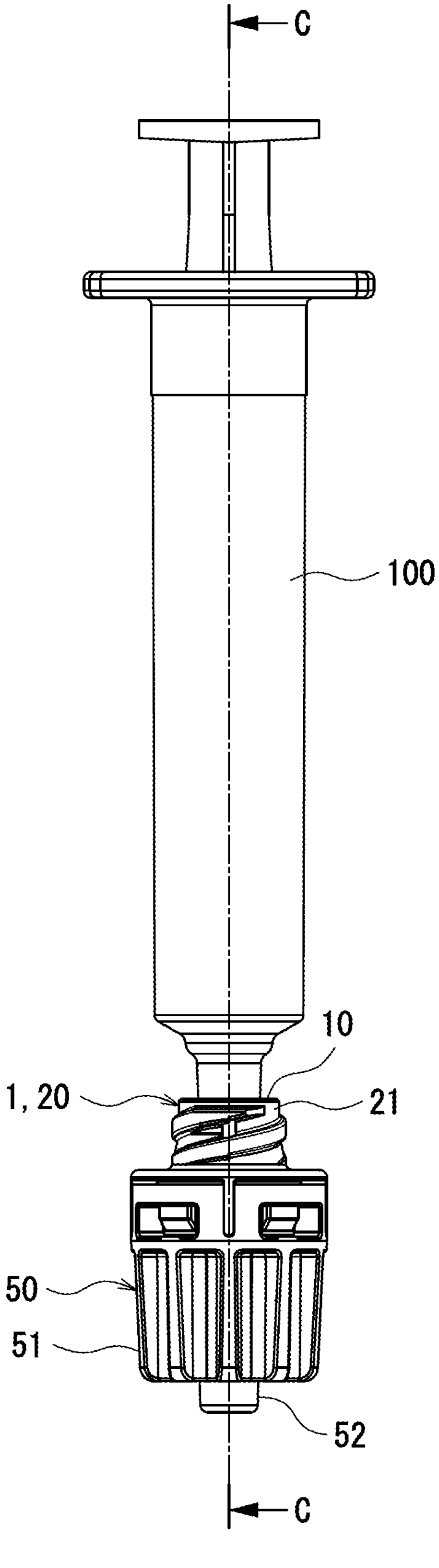
FIG. 5 is a view illustrating a state in which a syringe is connected to the medical connector according to the first embodiment.

Hereinafter, a male connector connection form of the medical connector 1 having the above-described configuration will be described with reference to FIGS. 5 and 6. Here, as an example of the male connector, the syringe 100 having a male luer without a metal needle is illustrated. FIG. 5 is a view illustrating a state in which the syringe 100 is connected, and FIG. 6 is a cross-sectional view taken along line CC in FIG. 5.

Figure 6:
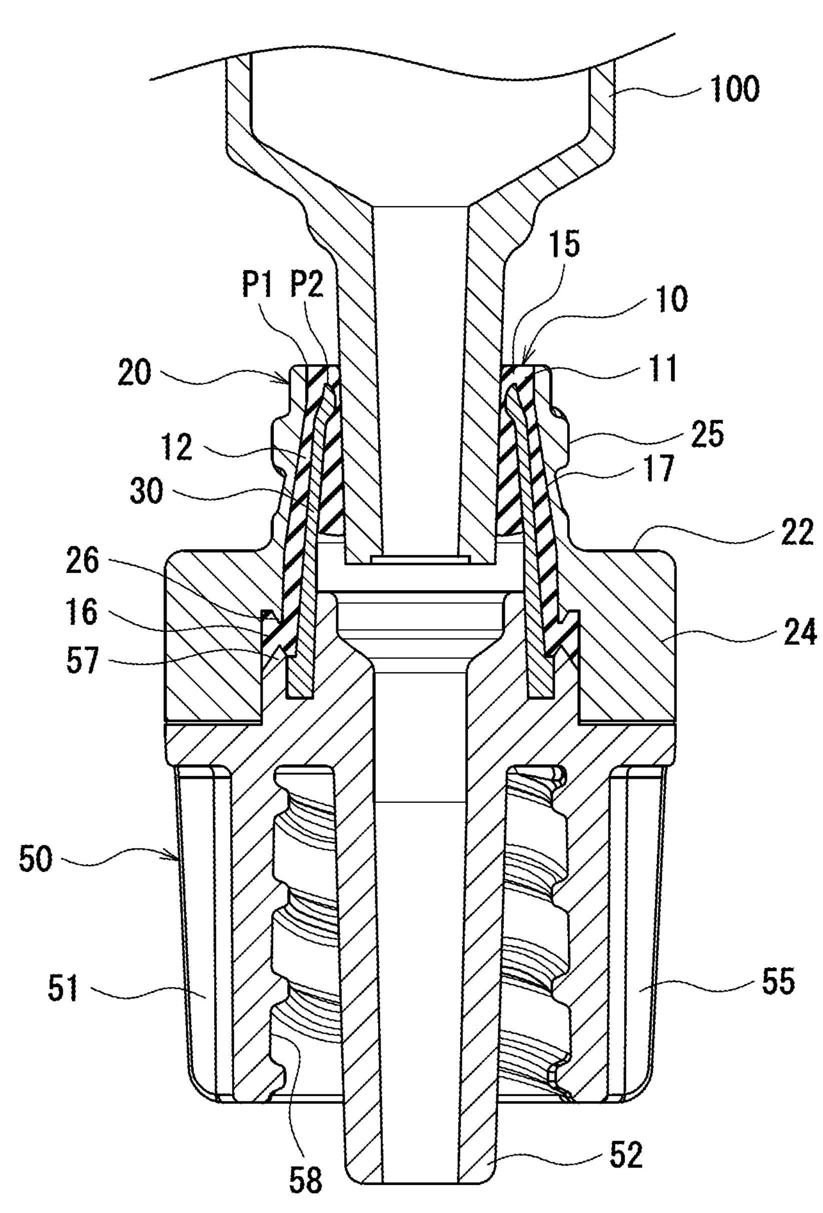
FIG. 6 is a cross-sectional view taken along line CC in FIG. 5.

As illustrated in FIGS. 5 and 6, a connection state in which the syringe 100 and the inside of the medical plug 5 communicate with each other is obtained by inserting a distal end portion of the syringe 100 into the slit 13 of the valve body 10. When the distal end portion of the syringe 100 is inserted into the slit 13, the valve body 10 is pushed downward and elastically deformed, the slit 13 is opened, and the distal end portion of the syringe 100 is introduced into the cylindrical internal housing 30. The distal end portion of the syringe 100 is inserted, for example, to the vicinity of the upper end of the inner cylindrical portion 52. A medicinal solution in the syringe 100 passes through the inside of the inner cylindrical portion 52 and is supplied to a fluid path such as an intravenous line to which the medical plug 5 is connected, or a blood circuit for dialysis.

When the distal end portion of the syringe 100 is inserted into the slit 13 and the valve body 10 is pushed downward, the thin portion 15 of the valve body 10 is bent, and a portion surrounded by the thin portion 15 enters the cylindrical internal housing 30. At this time, the slit 13 is opened, and the distal end portion of the syringe 100 is introduced into the cylindrical internal housing 30. Since there is a large gap between the valve main body portion 11 and the internal housing 30, contact between the valve body 10 and the internal housing 30 is suppressed at least at the initial stage of insertion of the syringe 100, and the insertion resistance of the syringe 100 is reduced. In addition, a radially inward load generated at the bonding portion 17 is reduced, and durability of the valve body 10 is improved.

Since the valve main body portion 11 is supported from the inner side by the internal housing 30 and the upper end portion thereof is bonded to the external housing 20, even when the valve main body portion 11 is pressed downward by the syringe 100, the entire valve body 10 does not fall into the cylindrical internal housing 30. A pressing force of the syringe 100 is applied to the thin portion 15 as described above, and the thin portion 15 is bent. At this time, although a certain degree of force is also applied to the bonding portion 17 between the valve body 10 and the external housing 20, since the bonding portion 17 is positioned outside the thin portion 15 in the radial direction of the medical connector 1, hardly any pressing force is applied to the bonding portion 17, and separation of the bonding portion 17 is suppressed. That is, as the bonding portion 17 is separated from the syringe, deformability of the valve body 10 is improved, and the load on the bonding portion 17 generated when the male connector is connected is reduced. In addition, the pressing force is applied to the upper end P2 of the internal housing 30 that supports the thin portion 15, and the internal housing 30 bears the pressing force. Therefore, compared with a case where the outer edge of the portion of the valve body 10 exposed to the outside is positioned at the same position as the upper end of the internal housing 30 in the radial direction, the pressing force of the syringe 100 applied to the bonding portion 17 is reduced.

With the medical connector 1, since an outer surface of the upper end of the outer circumferential surface of the valve body 10 is bonded to the inner circumferential surface of the external housing 20 even when the syringe 100 is connected, the bonding area can be increased, and a state of holding the valve body 10 is stably maintained. Even in a state where bonding between the valve body 10 and the external housing 20 is maintained, the connection of the syringe 100 is not hindered, and a favorable connection operation can be performed. In the present embodiment, since the bonding portion 17 is formed along the upper end P of the outer circumferential surface of the valve body 10, in other words, along the outer edge of the upper surface of the valve main body portion 11, infiltration of a medicinal solution or the like into the space between the valve body 10 and the external housing 20 is highly suppressed, and the medical connector 1 can be kept in a sanitary state.

In the first embodiment, the bonding portion formed between the valve body and the external housing is positioned outside the upper end of the internal housing in the radial direction of the connector, the extension portion (lower extension portion) of the valve body is formed, and the outer circumferential surface of the extension portion and the inner circumferential surface of the external housing are bonded to each other. However, any one of the configurations can be omitted as long as the object of the present invention is not impaired. However, in a case where both the configurations are provided, it is easy to implement the above-described effects compared with a case where only one of the configurations is provided (the same applies to a second embodiment).

Second Embodiment

Figure 7:
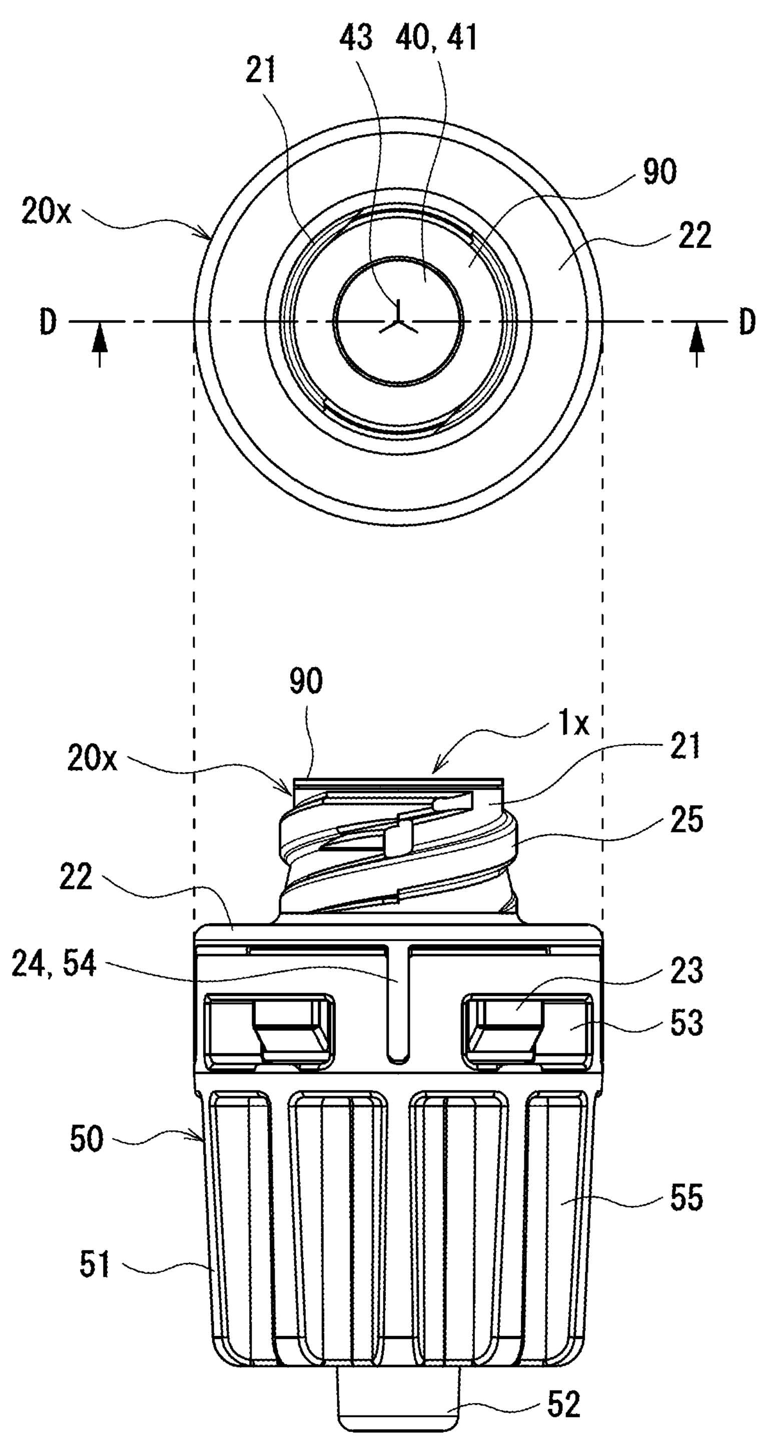
FIG. 7 is a plan view and a front view of the medical connector according to the second embodiment.
Figure 8:
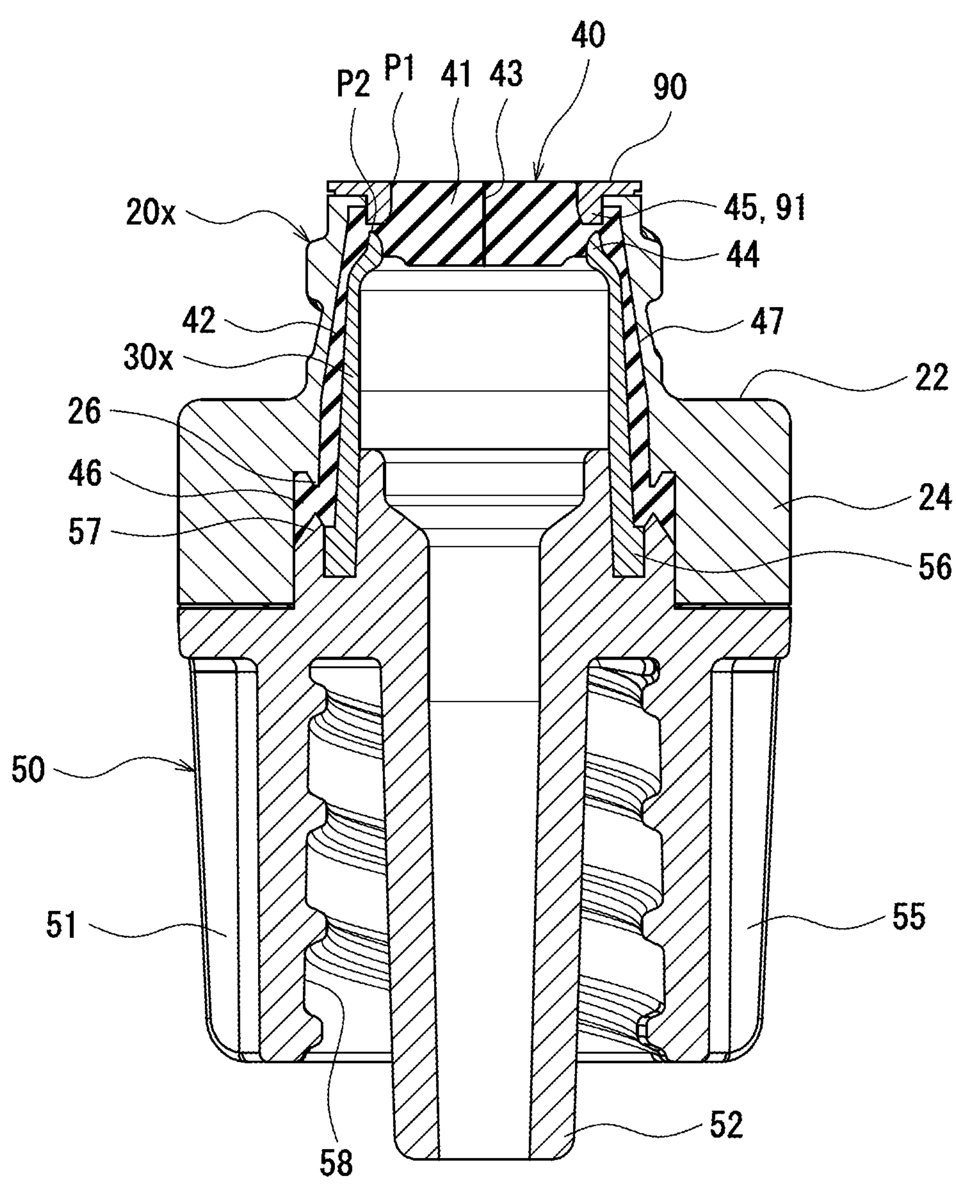
FIG. 8 is a cross-sectional view taken along line DD in FIG. 7.

A medical connector 1*x* according to the second embodiment will be described in detail below with reference to FIGS. 7 to 9. FIG. 7 is a plan view and a front view of the medical connector 1*x*, and FIG. 8 is a cross-sectional view taken along line DD in FIG. 7. Hereinafter, the same reference numerals are used for the configurations common to the first embodiment, and any overlapping description will be omitted.

As illustrated in FIGS. 7 and 8, the medical connector 1*x* is similar to the medical connector 1 in that the medical connector 1*x* includes a valve body 40, an external housing and an internal housing 30*x*. In addition, a connection structure between the medical connector 1*x* and the plug base 50 is the same as that of the medical connector 1, and the external housing 20*x* is provided with a locking claw 23 that engages with the opening portion 53 of the plug base 50. Similarly to the medical connector 1, the medical connector 1*x* has a structure in which the valve body 40 is arranged inside the external housing 20*x*, the internal housing 30*x* is arranged inside the valve body 40, and the valve body 40 is sandwiched between the external housing 20*x* and the internal housing 30*x*.

The valve body 40 includes a valve main body portion 41 in which a slit 43 is formed, a substantially cylindrical lower extension portion 42*a* extending downward from an outer circumferential portion of the valve body, and an upper extension portion 42*b* extending upward from the outer circumferential portion of the valve body, and is housed in the cylindrical external housing 20*x*. A lower groove 44 is formed in a lower surface of the valve body 40, and an upper end portion of the internal housing 30*x* is inserted into the lower groove 44. A projection 46 projecting radially outward is formed at a lower end portion of the lower extension portion 42*a*, and the projection 46 is pressed from above and below by a protrusion 26 of the external housing 20*x* and the protrusion 57 of the plug base Although a lower portion of the valve main body portion 41 is inserted into the cylindrical internal housing 30*x*, an outer circumferential surface of the valve main body portion 41 and an inner circumferential surface of the internal housing 30*x* are not bonded to each other.

The valve body 40 is preferably formed of, for example, silicone rubber, and is integrally molded with the external housing 20*x*. By adopting an aspect in which the valve body 40 is integrally molded with only the external housing 20*x*, an intermediate member to which the valve body 40 and the external housing 20*x* are bonded is formed, and then a pressing member 90 and the internal housing 30*x* are coupled, air bubbles are less likely to be generated on a bonding surface, and separation of the bonding surface can be prevented. The generation of air bubbles on the bonding surface is likely to cause the separation, but in the present embodiment, air bubbles are less likely to be generated on the bonding surface, so that a high bonding strength can be secured. Since upper ends of the valve body 40 and the internal housing 30 can be brought into a state where the valve body and an inner surface of the pressing member 90 are not bonded to each other, the valve body 40 has favorable mobility, and a resistance when the male connector is inserted can be reduced.

The medical connector 1*x* is different from the medical connector 1 in that the pressing member 90 fixed to an upper end portion of the external housing 20*x* is provided. The pressing member 90 presses the valve body 10 from above and holds the valve body between the pressing member 90 and the internal housing 30*x*. The pressing member is an annular member arranged in such a way as to surround an upper surface of the valve body 40 in plan view. In the medical connector 1*x*, an upper surface of the pressing member 90 is flat and is flush with the upper surface of the valve body 40. An outer diameter of the pressing member 90 is substantially the same as an outer diameter of an upper end of the external housing 20*x*.

The valve body 40 has an upper groove 45 into which a part of the pressing member 90 is inserted, and the upper extension portion 42*b* extends in such a way as to face an outer circumferential surface of the valve main body 41 with the upper groove 45 interposed therebetween. As described above, an outer circumferential surface of the valve body 40 and an inner circumferential surface of the external housing 20*x* are bonded to each other, but an outer circumferential surface of the upper extension portion 42*b* including an apex (upper end) of the upper extension portion 42*b* is preferably bonded to the inner circumferential surface of the external housing 20*x*. In this case, even when the valve body 40 is pushed downward by the syringe 100 or the like and elastically deformed, extension of the upper extension portion 42*b* is suppressed, and the upper extension portion 42*b* is sufficiently suppressed from coming off the pressing member 90 and falling inward.

A portion of the valve body 40 where the lower groove 44 and the upper groove 45 are formed is thin. Further, the upper groove 45 is formed at a position overlapping the lower groove 44 in the vertical direction in the upper surface of the valve body 40, and a constricted portion having a smaller thickness due to being constricted from opposite sides in the vertical direction is formed at the portion where the lower groove 44 and the upper groove 45 are formed. The constricted portion of the valve body 40 is pressed from above and below by the pressing member 90 and the internal housing 30*x*.

In the medical connector 1*x*, similarly to the medical connector 1, the external housing 20*x* and the valve body 40 are molded by insert molding or multicolor molding, and the external housing 20*x* and the valve body 40 are bonded. For example, in the medical connector ix, the external housing 20*x* to be bonded to a resin and nested components for forming the shape of the valve body 40 without being bonded to the resin are placed in an injection molding mold, and the resin is injected. The resin is injected from the inside toward the external housing 20*x* and flows from a filling space (a thin portion of the valve body 40) between the nested components into a filling space (the extension portion of the valve body 40) between the nested component and the external housing 20*x*. That is, the upper extension portion 42*b* of the valve body 40 is molded by a plurality of members such as the nested component and the external housing 20*x*, and the lower extension portion 42*a* is also molded by a plurality of members such as the nested component and the external housing 20*x*. It is easy to make a minute gap between the plurality of members through which gas passes but resin cannot pass. Therefore, when the resin is poured into the filling space for forming each extension portion, gas present in the filling space can be removed from the minute gap between the external housing 20*x* and the nested component. Therefore, air bubbles are less likely to remain at a portion to be bonded, the bonding area can be increased, and a possibility of air bubbles causing the separation can be reduced.

In the present embodiment, an annular protruding portion extending inward is formed at the upper end of the external housing 20*x* and is formed in an L shape in a cross-sectional view. Regarding the extension portion of the valve body 40, the length of the upper extension portion 42*b* is less likely to be larger than that of the lower extension portion 42*a*, and a bonding strength of the upper extension portion 42*b* is thus lower than that of the lower extension portion 42*a*. However, since the upper end of the external housing 20*x* is formed in an L shape, the bonding area can be increased. An upper end of the upper extension portion 42*b* is formed to be substantially flat and is bonded to the annular protruding portion. That is, the upper end (apex) of the upper extension portion 42*b* is not biased toward either the radially inner side or the radially outer side of the extension portion, the apex of the upper extension portion is formed outside the center of the upper extension portion in a width direction, and the apex is bonded to the external housing. In this case, it is possible to more effectively prevent the upper extension portion 42*b* from coming off the pressing member 90 and falling. The upper end of the upper extension portion 42*b* may be non-flat, the upper end (apex) of the upper extension portion 42*b* may be biased radially outward from the center in the width direction based on the center in the width direction at a base of the extension portion, and the apex of the upper extension portion may be formed outside the center in the width direction of the upper extension portion.

A portion where the annular protruding portion extending radially inward in the external housing 20*x* is provided is not limited to the upper end of the external housing 20*x*, and the annular protruding portion may be provided at any portion where it is desired to strengthen the bonding. In the present embodiment, the upper end of the external housing 20*x* is molded in an L shape, but in this case, minute air bubbles may remain in the vicinity of the bending point. Therefore, it is also possible to eliminate the annular protruding portion extending inward and form a shape in which air bubbles are less likely to remain. In this case, the pressing member 90, or the valve body 40, may be positioned in a space from which the annular protruding portion is eliminated.

The lower extension portion 42*a* is formed in a substantially cylindrical shape similarly to the extension portion 12 of the valve body 10, and preferably extends downward from the valve main body portion 41 from the viewpoint of increasing the bonding area with the external housing 20*x*. A length of the lower extension portion 42*a* in the vertical direction is larger than a length of the center of the valve main body portion 41 in the vertical direction. The lower extension portion 42*a* is longer than a width dimension (diameter) of a portion of the valve body 40 on an inner side of the constricted portion. The lower extension portion 42*a* and the upper extension portion 42*b* are formed in a substantially cylindrical shape on an outer circumferential side of the valve body 40 outside the constricted portion, and form the outer circumferential surface of the valve body 40 bonded to the external housing 20*x*.

The pressing member 90 is formed of a hard resin material, and is preferably formed of the same type of resin as the external housing 20*x*. The pressing member 90 is bonded to the upper end portion of the external housing 20*x* by, for example, ultrasonic welding. A welding projection protruding downward before ultrasonic welding is formed on a circumferential edge portion of the pressing member 90, and a lower surface of the pressing member 90 and the upper surface of the external housing 20*x* are integrated by melting the welding projection. The welding projection is formed in an annular shape in a circumferential direction of the pressing member 90.

In the pressing member 90, a projection 91 protruding downward is formed radially inside a bonding portion with the external housing 20*x*. The projection 91 largely protrudes downward and is formed in an annular shape along an inner edge of the pressing member 90. The projection 91 is arranged in such a way as to vertically overlap with an upper end P2 of the internal housing 30*x*. The upper end portion of the internal housing 30*x* is inserted into the lower groove 44 of the valve body 40, and the projection 91 of the pressing member 90 is inserted into the upper groove 45.

An inner diameter of the pressing member 90 is smaller than a diameter of the internal housing 30*x* at the upper end P2, and an upper end P1 of the outer circumferential surface of the valve main body portion 41 (an outer edge of a portion of the valve body 40 exposed to the outside) is positioned inside the upper end P2 in the radial direction of the medical connector ix. Although an inner circumferential surface of the pressing member is substantially in contact with the outer circumferential surface of the valve main body portion 41, the pressing member 90 is arranged in such a way as to surround the upper surface of the valve body 40 in plan view in a state of not being bonded to the valve body Since the pressing member 90 and the internal housing 30*x* are coupled to the intermediate member obtained by molding the external housing and the valve body, the pressing member 90 and the internal housing 30*x* are not bonded to the valve body 40.

As described above, the valve body 40 is not bonded to the pressing member 90, but the outer circumferential surface of the valve body 40 and the inner circumferential surface of the external housing 20*x* are bonded to each other. The valve body 40 and the external housing 20*x* are preferably configured as an integrally molded product (Z), and the entire outer circumferential surface of the valve body 40 in contact with the external housing 20*x* corresponds to the bonding portion 47. Since the external housing 20*x* has a simple shape without a U-shaped portion in a cross-sectional view at a bonding part with the valve body 40, a more favorable valve body 40 without air bubbles can be obtained when the valve body 40 and the external housing 20*x* are integrally molded. The bonding portion 47 has, for example, a substantially constant bonding strength over the entire region. Also in the medical connector 1*x*, an upper end of the bonding portion 47 is positioned radially outside the upper end P2 of the internal housing 30*x*, but the upper end P1 of the outer circumferential surface of the valve main body portion 41 is positioned radially inside the upper end P2.

Figure 9:
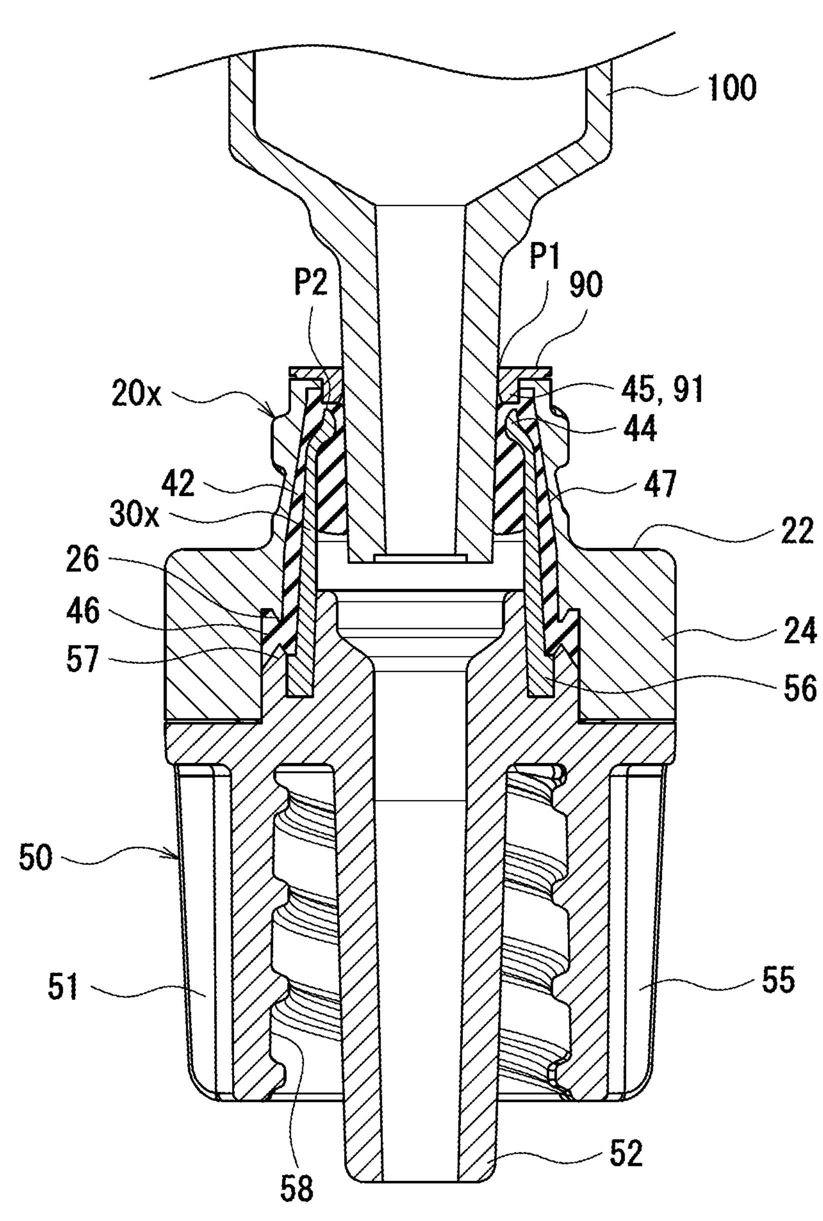
FIG. 9 is a cross-sectional view illustrating a state in which a syringe is connected to the medical connector according to the second embodiment.

As illustrated in FIG. 9, the syringe 100 is connected to the medical connector ix by inserting a distal end portion of the syringe 100 into the slit 43 of the valve body 40. When the distal end portion of the syringe 100 is inserted into the slit 43, the valve body 40 is pushed downward and elastically deformed, and the slit 43 is opened. When the distal end portion of the syringe 100 is inserted into the slit 43 and the valve body 40 is pushed downward, the valve main body portion 41 is bent at the thin portion sandwiched between the pressing member 90 and the internal housing 30*x*, and a portion surrounded by the thin portion enters the cylindrical internal housing 30*x*. At this time, the slit 43 is opened, and the distal end portion of the syringe 100 is introduced into the cylindrical internal housing 30*x*.

In the medical connector 1*x*, since the outer circumferential surface of the valve body 40 is bonded to the inner circumferential surface of the external housing 20*x*, a circumferential edge portion of the valve body 40 is prevented from falling inside the medical connector 1*x* when the syringe 100 is connected. Since the upper end of the bonding portion 47 is positioned radially outside the thin portion of the valve main body portion 41 that is bent when the syringe 100 is connected, a pressing force of the syringe 100 is hardly applied to the bonding portion 47, and separation of the bonding portion 47 is suppressed.

In addition, since the pressing member 90 is not bonded to the valve body 40, elastic deformation of the valve body 40 at the time of connecting the syringe 100 is not hindered. Therefore, it is possible to perform an excellent connection operation for the syringe 100 while preventing the valve body 40 from falling.

In the second embodiment, the constricted portion of the valve body 40 is pressed from above and below by the projection 91 of the pressing member 90 and the internal housing 30*x*, but it is possible to provide an engagement projection that presses the valve body 40 from above in the external housing and omit the pressing member. The internal housing that supports the lower surface of the valve body and the upper extension portion of the valve body are important components in suppressing the coming-off of the valve body, but any one of the configurations can be omitted as long as the object of the present invention is not impaired. However, in a case where both the configurations are provided, it is easy to implement the above-described effects compared with a case where only one of the configurations is provided.

The above-described embodiments can be appropriately modified in design without impairing the object of the present invention. For example, in the above-described embodiments, the valve body 10 including the cylindrical extension portion 12 extending from the circumferential edge portion of the valve main body portion 11 has been exemplified, but the valve body does not have to include the extension portion 12. The valve body may have a disk shape as disclosed in JP 2016-028753 A. In addition, the locking claw 23 and the projection 24 do not have to be formed in the external housing of the medical connector. A medical connector 1*y* illustrated in FIGS. 10 and 11 includes an external housing 20*y* having a cylindrical large-diameter portion 22*y*.

Figure 10:
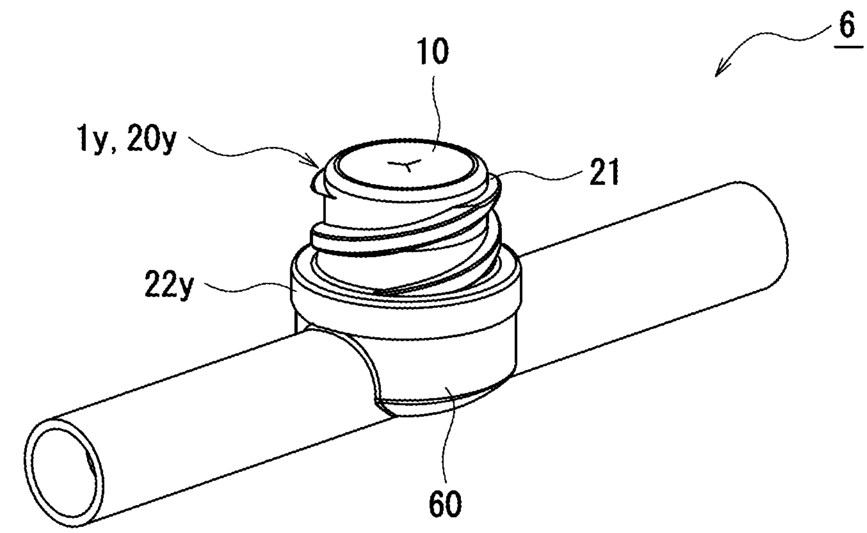
FIG. 10 is a diagram illustrating another application example of the medical connector.
Figure 11:
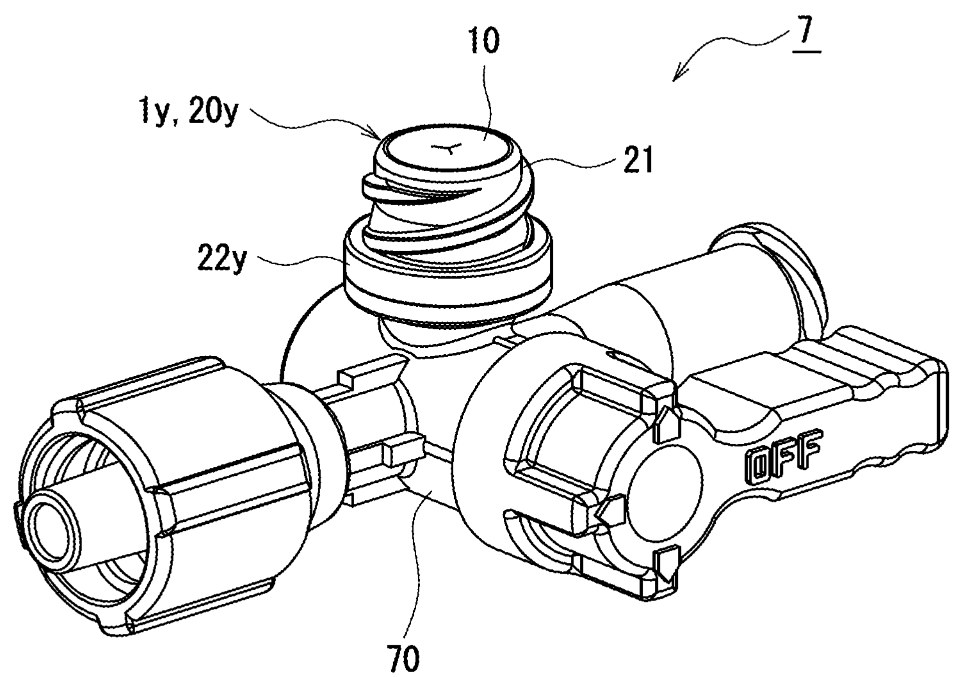
FIG. 11 is a diagram illustrating another application example of the medical connector.

In the example illustrated in FIG. 10, the medical connector 1*y* is attached to a T-shaped tube base 60, and a T-shaped co-injection tube 6 including the medical connector 1 and the T-shaped tube base 60 is configured. The large-diameter portion 22*y* of the external housing 20*y* may be bonded to the T-shaped tube base 60 by ultrasonic welding or the like, or may be fixed by screw fitting by forming a screw on the inner circumferential surface. In the example illustrated in FIG. 11, the medical connector 1*y* is attached to a three-way stopcock base 70, and a three-way stopcock 7 including the medical connector 1*y* and the three-way stopcock base 70 is configured.

REFERENCE SIGNS LIST

1, 1*x*, 1*y* Medical connector
5 Medical plug
6 T-shaped co-injection tube
7 Three-way stopcock
10, 40 Valve body
11, 41 Valve main body portion
12 Extension portion
13, 43 Slit
14 Groove
15 Thin portion
16, 24, 46 Projection
17, 47 Bonding portion
20, 20*x*, 20*y* External housing
21 Small-diameter portion
22, 22*y* Large-diameter portion
23 Locking claw
25 Screw thread
26, 57 Protrusion
30, 30*x* Internal housing
31 Step
42*a* Lower extension portion
42*b* Upper extension portion
44 Lower groove
45 Upper groove
50 Plug base
51 Outer cylindrical portion
52 Inner cylindrical portion
53 Opening portion
54 First groove
55 Recess
56 Second groove
58 Lock groove
60 T-shaped tube base
70 Three-way stopcock base
90 Pressing member
91 Projection
100 Syringe

The invention claimed is:

1. A medical connector comprising:
a valve body in which a slit is formed;
a cylindrical external housing that houses the valve body and holds the valve body; and
a cylindrical internal housing that is inserted into the cylindrical external housing and supports a lower surface of the valve body,
wherein a bonding portion is formed between the valve body and the external housing, and
the bonding portion is positioned outside an upper end of the internal housing in a radial direction of the connector,
wherein an outer circumferential surface of the valve body is bonded to an inner circumferential surface of the external housing by the bonding portion.

2. The medical connector according to claim 1,
wherein a groove into which an upper end portion of the internal housing is inserted is formed in the lower surface of the valve body, and
the groove is formed on an inner side of an outer edge of a top portion of the valve body exposed to the outside, the inner side is defined in the radial direction of the connector.

3. The medical connector according to claim 1,
wherein the bonding portion is disposed at least at an upper end of the outer circumferential surface of the valve body.

4. A medical connector comprising:
a valve body in which a slit is formed;
a cylindrical external housing that houses the valve body and holds the valve body;
a pressing member that is fixed to an upper end portion of the external housing; and a cylindrical internal housing that is inserted into the cylindrical external housing and supports a lower surface of the valve body, wherein an outer circumferential surface of the valve body and an inner circumferential surface of the external housing are bonded to each other by insert molding or multicolor molding, and the pressing member is arranged in such a way as to surround an upper surface of the valve body in plan view.

5. The medical connector according to claim 4, wherein a groove into which an upper end portion of the internal housing is inserted is formed in the lower surface of the valve body, and the groove is formed on an inner side of an outer edge of a portion of the valve body exposed to the outside, the inner side is defined in the radial direction of the connector.

6. A medical connector comprising:

a valve body in which a slit is formed;

a cylindrical external housing that houses the valve body and holds the valve body; and a cylindrical internal housing that is inserted into the cylindrical external housing and supports a lower surface of the valve body, wherein the valve body includes a valve main body portion in which the slit is formed and an extension portion extending downward beyond a lower end of the valve main body portion and positioned between the external housing and the internal housing, and an outer circumferential surface of the extension portion and an inner circumferential surface of the external housing are bonded to each other.

7. The medical connector according to claim 6, wherein a groove into which an upper end portion of the internal housing is inserted is formed in the lower surface of the valve body, and the groove is formed on an inner side of an outer edge of a portion of the valve body exposed to the outside, the inner side is defined in the radial direction of the connector.

8. A medical connector comprising:

a valve body in which a slit is formed;

a cylindrical external housing that houses the valve body and holds the valve body;

a pressing member that is fixed to an upper end portion of the external housing; and a cylindrical internal housing that is inserted into the cylindrical external housing and supports a lower surface of the valve body, wherein an outer circumferential surface of the valve body and an inner circumferential surface of the external housing are bonded to each other, and a part of the valve body is inserted into the cylindrical internal housing, and the outer circumferential surface of the valve body and an inner circumferential surface of the internal housing are not bonded to each other.

9. The medical connector according to claim 8, wherein a groove into which an upper end portion of the internal housing is inserted is formed in the lower surface of the valve body, and the groove is formed on an inner side of an outer edge of a portion of the valve body exposed to the outside, the inner side is defined in the radial direction of the connector.

10. A medical connector comprising:

a valve body in which a slit is formed; and a cylindrical housing that houses the valve body and holds the valve body, wherein an engagement projection is provided at an upper end portion of the external housing, the valve body includes a valve main body in which the slit is formed, an upper groove into which the engagement projection is inserted, and an upper extension portion extending in such a way as to face an outer circumferential surface of the valve main body with the upper groove interposed therebetween, an apex of the upper extension portion is formed outside a center of the upper extension portion in a width direction, and an outer circumferential surface of the upper extension portion and an inner circumferential surface of the external housing are bonded to each other.

11. The medical connector according to claim 10, wherein a groove into which an upper end portion of the internal housing is inserted is formed in the lower surface of the valve body, and the groove is formed on an inner side of an outer edge of a portion of the valve body exposed to the outside, the inner side is defined in the radial direction of the connector.

* * * * *